(12) United States Patent
Craus et al.

(10) Patent No.: US 9,108,220 B2
(45) Date of Patent: Aug. 18, 2015

(54) DEVICE FOR FRANMENTING MOLECULES IN A SAMPLE BY ULTRASOUND

(75) Inventors: Cristian Bogdan Craus, Eindhoven (NL); Jacob Marinus Jan Den Toonder, Eindhoven (NL); Roel Penterman, Eindhoven (NL); Pieter Jan Van Der Zaag, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/117,378

(22) PCT Filed: Jun. 5, 2012

(86) PCT No.: PCT/IB2012/052812
§ 371 (c)(1),
(2), (4) Date: Nov. 13, 2013

(87) PCT Pub. No.: WO2012/168853
PCT Pub. Date: Dec. 13, 2012

(65) Prior Publication Data
US 2014/0193305 A1     Jul. 10, 2014

(30) Foreign Application Priority Data
Jun. 6, 2011  (EP) .................................... 11168824

(51) Int. Cl.
| G01N 15/06 | (2006.01) |
| G01N 33/00 | (2006.01) |
| G01N 33/48 | (2006.01) |
| B06B 3/00 | (2006.01) |
| B02C 19/18 | (2006.01) |
| C12M 1/00 | (2006.01) |
| G01N 1/28 | (2006.01) |

(52) U.S. Cl.
CPC . *B06B 3/00* (2013.01); *B02C 19/18* (2013.01); *C12M 47/06* (2013.01); *G01N 1/286* (2013.01); *Y10T 29/49826* (2015.01)

(58) Field of Classification Search
USPC ........................... 422/50, 68.1, 554, 502, 503
See application file for complete search history.

(56) References Cited

U.S. PATENT DOCUMENTS

| 5,126,616 | A | 6/1992 | Gorton et al. |
| 7,625,746 | B2 | 12/2009 | Patno et al. |
| 2002/0039783 | A1 | 4/2002 | McMillan et al. |
| 2002/0187547 | A1 | 12/2002 | Taylor et al. |
| 2003/0005771 | A1 | 1/2003 | Percin et al. |

FOREIGN PATENT DOCUMENTS

| EP | 0353365 A2 | 2/1990 |
| WO | 2004034436 A2 | 4/2004 |
| WO | 20100121144 A1 | 10/2010 |
| WO | 2011048521 A1 | 4/2011 |

*Primary Examiner* — Brian J Sines

(57) ABSTRACT

According to an aspect of the present invention, a device for fragmenting molecules in a sample by ultrasound is provided. The device comprises a planar-shaped cartridge and a fragmentation instrument that has a vessel-like shape. By means of applying under-pressure in the fragmentation instrument the cartridge is pulled towards the fragmentation instrument and therefore spatially closes a fluid compartment that is comprised by the fragmentation instrument. Afterwards, an ultrasound treatment of the sample, which is comprised in a sample compartment of the cartridge, may be processed. A sealing layer is provided in between the cartridge and the fragmentation instrument in order to hold the fixation of the cartridge tightly and in order to provide for leakage prevention out of the fluid compartment.

12 Claims, 11 Drawing Sheets

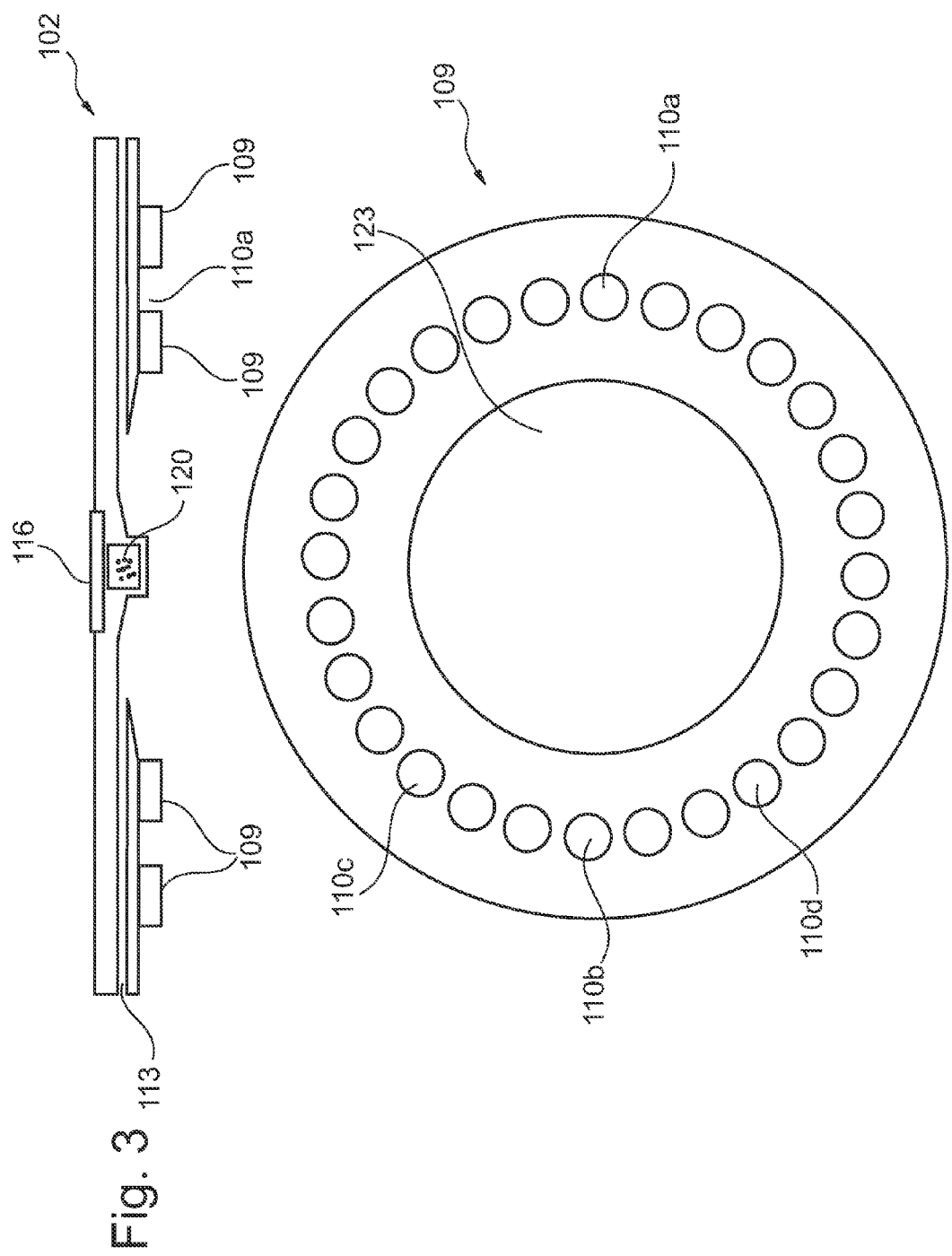

|     | Duration (min) | $T_{start}$ (°C) | $T_{stop}$ (°C) |
| --- | --- | --- | --- |
| #1  | 2 | 20.3 | 40 |
| #2  | 3 | 21.2 | 33 |
| #3  | 4 | 22.2 | 61 |
| #4  | 5 | 23.8 | 62 |

Fig. 7

DEVICE FOR FRANMENTING MOLECULES IN A SAMPLE BY ULTRASOUND

CROSS-REFERENCE TO PRIOR APPLICATIONS

This application is the U.S. National Phase application under 35 U.S.C. §371 of International Application Serial No. PCT/IB2012/052812, filed on Jun. 5, 2012, which claims the benefit of Application Serial No. EP 11168824.8, filed on Jun. 6, 2011. These applications are hereby incorporated by reference herein.

FIELD OF THE INVENTION

The present invention relates to the interfacing of a cartridge with an ultrasound transducer. In particular, the present invention relates to a device for fragmenting molecules in a sample by ultrasound. Further, the present invention relates to a fragmentation instrument and a cartridge for fragmenting molecules in a sample by ultrasound. Moreover, the present invention relates to a method for providing an ultrasound device for fragmenting molecules in a sample.

BACKGROUND OF THE INVENTION

The continually dropping costs of sequencing have opened the possibilities of clinically using DNA sequencing, apart from the traditional field of clinical genetics, in oncology as well as in other fields like plant breeding, pathogen detection as well as fields of research.

At the moment most commercial instruments for sequencing and the ones in development as next generation have an only partly automated procedure. The detection of the bases in each strand is performed and the resulting reads of the DNA are outputted. Largely, the sample preparation before the sequencing procedure itself is still performed by trained personnel. In this way significant time and resources are being spent. The time line of a present sequencing run spans usually over three weeks, of which one week is the sample preparation, another week is the automated detection of bases of DNA strands and one week is needed for bio-informatics analysis.

After the extraction of the DNA from the cells the molecules have to be fragmented before the detection of the bases starts to take place on the same cartridge. It is preferable that the average size of the DNA strands is approximately 200 base pairs (bp). This particular length is equal with the ideal read length required in the computational analysis. It is clear that the minimum amount of required DNA material (from biopsies for instance) can be reduced significantly if the fragmentation procedure leads to average size of the molecules $L_{AVG}$ that is as close as possible to the ideal read length. Furthermore it is preferable that $L_{AVG}$ can be tuned to a certain length depending on the minimum requirements of the following steps.

It should be noted that the commonly accepted method for selecting DNA fragments with proper length consists in the following steps: a) perform a given fragmentation method, b) run a gel electrophoresis experiment where a calibration ladder is placed, c) select the fragments at the proper length by cutting out the corresponding part of the gel. Alternatively an automated instrument can perform a similar operation with more reproducible results. Such device requires trained personnel and approximately one hour of processing.

EP 0 353 365 describes an ultrasonic cell-destroyer in which different solution containers are provided in a closure plate 21. US 2002/0039783 A1 describes a device for lysing cells, spores, or microorganisms. US 2002/0187547 A1 describes a container for holding cells for disruption.

From WO 2011048521 A1 microfluidic cartridge with a parallel pneumatic interface plate is known. Such a device makes it possible to move a liquid a long predefined path on a microfluidic cartridge.

Although there are several methods for DNA fragmentation only a few can be considered adequate for special purposes. However, all of them seem to have at least one disadvantage which needs to be improved. A few of these methods are mentioned herein. Firstly the enzymatic digestion is a method that is used in DNA fragmentation. The disadvantage of this method is that the places where the strands are cut are not randomly distributed. This can be a source of errors in the computational analysis. Secondly flow boundary layer method is a fluidic method for fragmentation. This method requires substantial pressures to be developed on the cartridge. The fluid containing the DNA molecules is passed through an orifice at very high flow rates Q on the order of hundreds of ml/min. For instance it has been reported that for $L_{AVG}$=1000 bp, Q=125 ml/min is required. The orifice used had the length L=1 mm and radius R=125 µm. The pressure difference developed in these conditions would have been $$p = \frac{8L\eta}{\pi R^4} Q = 350 \text{ MPa}.$$

It is clear that such method integrated in a cartridge would require unacceptable costs of fabrication due to the components to be used, e.g. shearing orifice made of ruby. Thirdly sonication is another method that can be successfully used for shearing DNA molecules. Indeed the method can have $L_{AVG}$~200 bp. It consists of immersing an ultrasound transducer or an acoustical wave guide into the sample fluid. Such procedure brings the risk of sample contamination and the minimum volumes to be used are in the order of hundreds of micro-liters. In addition the risk of foaming the sample is substantial when some buffers are used. Foaming can be easily obtained when trying to re-disperse beads sediment after long storage time. Also, sonication is not a solution for a sequencing system with a closed disposable cartridge. Fourthly the use of the principles of ultrasonic cavitation is known. Acoustic pressure fields are applied in order to trigger bubble nucleation followed by cavitation. As a result pressure gradients are created along the DNA molecules resulting in fragmentuation. The sample is placed in a closed container located in the focal region of an ultrasound transducer. Known devices using such cavitation can be used for sample volumes ranging from 50 µl to milliliters. Furthermore the known devices have active cooling to control the water bath in which the transducer is placed. A large water container (>25 cm×25 cm×25 cm) is required to accommodate the ultrasound transducer, the cooling circuit and the sample fixture. Due to its dimensions such device would be difficult or impossible to integrate in a sample-preparation station. Fifthly wind stress boundary layer and boundary-induced acoustic streaming is known for fragmentation. In this case the sample is placed in the proximity of an ultrasound transducer. In case solid material is present in the propagation path of ultrasound an inherent increase of the transducer temperature during a treatment and other physical parameters may occur. Therefore the impedance properties of the solid material may change from experiment to experiment leading to serious reproducibility issues.

SUMMARY OF THE INVENTION

Therefore, it may be seen as an object of the present invention to provide for an improved fragmenting of molecules by ultrasound.

The object is solved by the subject-matter as defined in the independent claims. Further aspects and advantages of the invention are defined in the dependent claims. The present invention addresses above described needs and provides means and methods for fragmenting molecules in a sample by ultrasound and provides means and methods for providing an ultrasound device for such a purpose.

It should be noted that features and advantages described herein with respect to the device should be understood as being simultaneously described with respect to the fragmentation instrument, the cartridge and the method and vice versa. Thereby, the person skilled in the art without any undue burden integrates features described for example with respect to the device into the fragmentation instrument, the cartridge and/or the method and vice versa.

According to a first aspect of the present invention, a device for treating or fragmenting molecules in a sample by ultrasound is presented. The device comprises a cartridge, a fragmentation instrument with an ultrasound transducer and a fluid compartment. Thereby, the cartridge comprises a sample compartment for including the sample with the molecules that need to be fragmented by ultrasound. Furthermore, the fluid compartment is especially separated from the sample compartment. The cartridge and the fragmentation instrument fit together in such a way that a spatial closure of the fluid compartment is established when the cartridge and the fragmentation instrument are assembled together. The established spatial closure may be an entire spatial closure of the fluid compartment.

As the fluid compartment may for example be filled with water for transmitting the emitted ultrasound energy from the transducer to the sample contained in the closed cartridge, the established closure of the fluid compartment may be a fluid-tight closure.

Therefore, the term "fluid compartment" may be understood as transmission fluid compartment. Moreover, the term "cartridge" may be understood in the context of the present invention as a disposable cartridge or as a microfluidic cartridge or as a disposable microfluidic cartridge.

Furthermore, the fluid compartment can be comprised by the cartridge or it can also be comprised by the fragmentation instrument. It may also be a component which is a separate element that needs to be assembled with the fragmentation instrument and/or the cartridge.

By assembling the fragmentation instrument and the cartridge together the sample compartment and thus the sample is automatically and/or inherently positioned in the focal spot and/or volume of the ultrasound transducer of the fragmentation instrument. As the fragmentation instrument is adapted to receive the cartridge and the cartridge is adapted to be inserted into the instrument they build a mechanical unit when they are assembled. However, they may be built of two separated physical parts. The assembly of the fragmentation instrument and the cartridge may for example be established by applying a vacuum or an under-pressure. However, also other fixation means like for example screws or magnetic forces may be used to establish the closure of the fluid compartment. Thereby, the closure is a spatial closure of the opening of the fluid compartment against the surrounding of the instrument. By placing the cartridge on the fragmentation instrument the fluid compartment becomes a closed volume in which fluid or any medium can be filled in so as to transmit ultrasound from the transducer to the sample in the cartridge. Therefore, the need may exist to provide for a fluid-tight closure or fluid-tight interfacing between the cartridge and the fragmentation instrument.

The fact, whether a cartridge and a fragmentation instrument fit together in the desired way can directly and positively verified by tests or procedures described herein and/or which are known to the person skilled in the art.

Furthermore, it does not need undue experimentation to verify whether the cartridge and the fragmentation instrument fit together in such a way that a spatial closure of the fluid compartment is established when the cartridge and the fragmentation instrument are assembled together.

The present invention allows for the integration of all sample preparation steps for DNA sequencing on one cartridge.

Further, the present invention provides for a solution for an interfacing of a closed cartridge (sequencing) with a fragmentation instrument and the integration of a fragmentation method in a platform used for DNA sequencing. In other words a device and a method for fragmentation of e.g. DNA molecules are proposed herein, addressing the cartridge integration and reproducibility issues mentioned above.

The present invention does not need an active cooling for the fragmentation of molecules, which simplifies the fragmentation process and may reduce effort and costs.

In the context of the present invention the transducer is not in the cartridge. The cartridge might be a disposable product out of e.g. a polymer material which is desirable in view of keeping the costs of the cartridge low. Thus, the cartridge according to the present invention may not comprise electronical and/or electrical components.

Furthermore, in the context of the present invention the term "molecules" shall be understood to comprise nucleic acids, DNA, RNA, tissue, biological sample, and pathological sample. However, the term "molecule" shall not be delimited to these examples.

According to an exemplary embodiment of the invention, the cartridge has a planar shape and the fragmentation instrument has a vessel-like shape.

In other words, a device for fragmenting molecules in a sample by ultrasound is provided wherein the fragmentation instrument is a vessel-like object comprising a vessel opening, which may be positioned e.g. opposite of the bottom of the fragmentation instrument.

Moreover, the cartridge is adapted to be a lid or a cover of the fragmentation instrument. The vessel-like fragmentation instrument can be fluid tightly closed and made viable for ultrasound processing upon placing the cartridge onto the fragmentation instrument. Thus only when the fragmentation instrument and the cartridge are assembled together a viable and working device may be provided.

While the sample is contained in the cartridge, several cartridges subsequently may be placed on the fragmentation instrument, wherein the respective cartridges respectively build a lid or closing cover for the fluid compartment of the fragmentation instrument. In between, several flushing processes like filling water into the fluid compartment, applying under-pressure or a vacuum to fix and stabilize the cartridge on the sidewalls of the fragmentation instrument may be applied. This will be described in more detail in the below description.

According to another exemplary embodiment of the invention, the fluid compartment comprises an opening and wherein the cartridge and the fragmentation instrument are respectively adapted to establish a closure of the fluid compartment in such a way that the opening of the fluid compartment is fluid-tightly sealed.

Thereby, the opening may be defined by the sidewalls of the fragmentation instrument which may be shaped as for example a tube. The contour of the sidewalls may build the boundaries of the opening as might be gathered from the below picture description.

Thereby, the opening is closed by placing, inserting and/or integrating the cartridge into the fragmentation instrument. For example, the cartridge may be integrated by sliding. Therefore, sliding means like e.g. sliding rails or tracks may be provided by the cartridge and/or by the fragmentation instrument. However, also a laying the cartridge onto the sidewalls of the housing of the fragmentation instrument with a simultaneously or subsequently applied under-pressure is possible.

According to another exemplary embodiment of the invention, the device further comprises a sealing layer in between the cartridge and the fragmentation instrument.

The sealing layer may be a soft layer that is elastically deformable like for example PDMS or a rubber material. Also other polymer or non-polymer materials may be used. The sealing layer may be part of the fragmentation instrument, may be part of the cartridge and/or may be a separate, third physical element. In one exemplary embodiment the soft sealing layer may be fixed on the cartridge and may also act as a membrane to actuate fluids. Such a soft rubber layer may be placed at the bottom of the cartridge.

According to another exemplary embodiment of the invention, the cartridge comprises a pump, wherein the pump is adapted of pumping a fluid into the fluid compartment.

According to another exemplary embodiment of the invention, the fragmentation instrument comprises a liquid inlet and the cartridge comprises an overflow channel.

This exemplary embodiment may be seen for example from FIG. 2. The cartridge together with the fragmentation instrument builds the fluid chamber which is provided in order to transmit ultrasound energy from the transducer to the sample. Therefore, liquid may be transported from outside of the fragmentation instrument into the fluid compartment via the liquid inlet. As an overflow or drain channel the cartridge, which has already been positioned on top of the fragmentation instrument provides for such a channel. Therefore, the combination of the fragmentation instrument and the cartridge together establish the whole process volume in order to be able to provide for fragmentation like e.g. DNA fragmentation.

According to another exemplary embodiment of the invention, the device comprises a temperature probe wherein the temperature probe is located at the sample compartment or in the fluid compartment.

According to another exemplary embodiment of the invention, the device comprises a sealing layer which is a flexible membrane, wherein the flexible membrane provides for the spatial closure of the fluid compartment. Furthermore the flexible membrane is adapted to actuate the sample comprised in the sample compartment when the transducer emits ultrasound, i.e. when the flexible membrane is radiated with ultrasound from the ultrasound transducer. The sample may remain in good thermal contact to the liquid below. Furthermore the acoustical impedance between the sample fluid in the sample compartment and the fluid in the fluid compartment, which fluid is in direct contact to the transducer, may not be significantly changed compared with a situation without such a membrane. In other words the sample chamber according to the present invention may hang directly in the fluid compartment.

In other words the flexible membrane is adapted to be movable up and down by e.g. ultrasound or a pneumatic force in order to actuate the sample. It should be noted that this movable part of the flexible membrane may be in a part of the cartridge which is separated from the sample compartment. In other words the device is adapted in such a way that the sample may be moved along the cartridge by the flexible membrane which is moved perpendicular or essentially perpendicular to the direction in which the fluid is pressed. Thus, the sample may be transportable into the sample compartment by translating the flexible membrane by various types of possible forces.

Therefore, the flexible membrane may be stretched to a specific extent in order to provide for a reset force in case the ultrasound is not pushing the flexible membrane into the sample compartment. Thus, the sealing layer is adapted to close the liquid compartment as a lid. With it's second parallel functionality as a actuation means the flexible membrane is able to apply mechanical pressure onto the sample as it may be positioned movable between the cartridge and ultrasound instrument.

According to another aspect of the present invention, a fragmentation instrument for fragmenting molecules in a sample by ultrasound is provided. The instrument comprises an ultrasound transducer, a fluid compartment, wherein the fluid compartment comprises an opening. The fragmentation instrument is adapted to receive a cartridge according to the below described aspect of the invention. Thereby, the cartridge comprises the sample. Furthermore, the fragmentation instrument is adapted to establish in combination with the cartridge an entire spatial closure of the opening of the fluid compartment upon receipt of the cartridge.

According to another aspect of the present invention, a cartridge for fragmenting molecules in a sample by ultrasound is presented. The cartridge comprises a sample compartment for including the sample with the molecules. Furthermore, the cartridge is adapted to be inserted in a fragmentation instrument according to the previously described aspect of the invention. The cartridge is adapted to establish in combination with the fragmentation instrument an entire spatial closure of the opening of the fluid compartment of the fragmentation instrument upon insertion of the cartridge.

In other words, by assembling the cartridge and the fragmentation instrument a viable and working device for fragmentation is provided.

According to another aspect of the present invention, a method for providing an ultrasound device for fragmenting molecules in a sample is presented. The method comprises the steps of providing for a device which comprises a fragmentation instrument, a cartridge and a fluid compartment. Thereby, the fluid compartment may be comprised by the fragmentation instrument or by the cartridge. It may also be a separate physical element which is subsequently affixed to one of the fragmentation instrument or the cartridge. The cartridge comprises a sample compartment which is spatially separated from the fluid compartment. The method further comprises the step of placing the cartridge onto the fragmentation instrument. Thereby, this step causes a closure of the fluid compartment as the third step of this method.

This method may also be seen as an interfacing method that may also be used in other areas of applications when a fluid is to be located outside of a disposable, e.g. for temperature regulation.

According to another exemplary embodiment of the invention, the method further comprises the step of applying an under-pressure between the cartridge and the fragmentation instrument and the further step of sucking the cartridge towards the instrument by means of the under-pressure is also provided. If desired, a seal layer may be provided between the fragmentation instrument and the cartridge.

According to another aspect of the present invention the cartridge comprises a soft layer which acts as a flexible membrane.

The flexible membrane may be provided in such a way that no ultra sound energy is absorbed. As an example one may use a thin membrane of 100 micrometer. This is thin compared to the mm-wavelength of an e.g. 1.7 MHz ultrasound wave in for example water that is filled in the fluid compartment. Hence the flexible membrane of the cartridge will not absorb much. Therefore a thin membrane may be desirable. In case, where the membrane is used as the actuation and sealing layer in the cartridge the thickness of the membrane may be 90-100 micrometers.

In other words the cartridge may have inter alia two options. The bottom layer of sample compartment 102 may be formed out of a hard plastic material or it might be formed of a soft membrane. In order to be able to decrease the thickness of a soft membrane the present invention may assure that the ultrasound focal region lies very well in the sample compartment, away from the flexible membrane.

Therefore e.g. a mixing procedure of the sample can be realized by ultrasound and by means of the flexible membrane which is placed between the sample and the transducer as a wall of the sample compartment of the cartridge.

It may be seen as a gist of the invention to provide for a cartridge containing a sample and a fragmentation instrument, wherein the cartridge is adapted to close a fluid compartment of the instrument in such a way that ultrasound waves can propagate through the fluid compartment towards the cartridge and treat molecules to be fragmented. An assembly of the cartridge and the fragmentation instrument may be established by applying under-pressure in order to suck the cartridge onto rims of the housing of the fragmentation instrument. A soft sealing layer may be provided in order to prevent fluid leakage out of the fluid compartment.

These and other features of the invention will become apparent from and elucidated with reference to the embodiments described hereinafter.

DESCRIPTION OF THE DRAWINGS

Exemplary embodiments of the invention will be described in the following drawings.

FIG. 3 schematically shows a cross-section of a cartridge according to an exemplary embodiment of the invention.

FIG. 4 schematically shows a top view of a sealing layer.

FIG. 7 schematically shows a table of parameters for experiments performed with a device according to an exemplary embodiment of the invention.

DETAILED DESCRIPTION OF EMBODIMENTS

Figure 1:
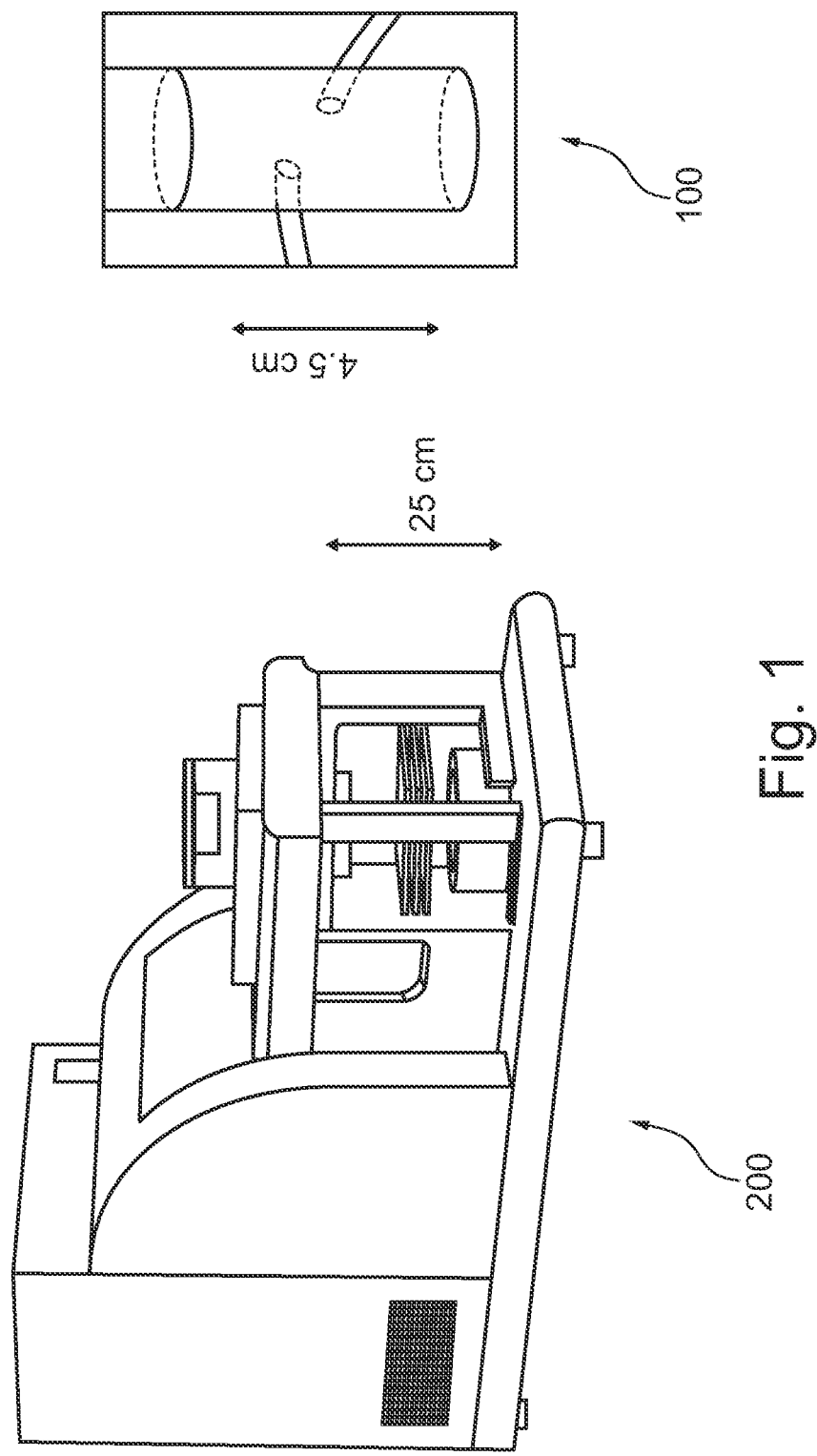
FIG. 1 schematically shows a comparison of size of a device according to the present invention with a device of the prior art.

FIG. 1 shows a comparison of size between a device 100 for fragmenting molecules in a sample by ultrasound according to the present invention and a device 200 of the prior art. It can clearly be seen that a size reduction is reached by the present invention as will be clearly described in the following description.

The overall size of the device according to the present invention may be decreased compared to the state of the art due to inter alia the following reasons. The effective volume within which the pressure conditions for fragmentation are satisfied may be comparable to the volume of the sample compartment. As an example a small PZT transducer with a diameter of approximately 2 cm can be used. The transducer may e.g. have a circular shape. The acoustic energy from the piezoelectric transducer may be focused on a pen like volume with a diameter of 2-3 mm and a length of 5 mm. If required, concentration or dilution steps of the DNA content can be performed in separate chambers on the cartridge prior the fragmentation procedure. Thus, the cartridge according to the present invention may comprise at least on additional compartment for preparing the sample before fragmenting it. Therefore the need of larger aqueous samples for DNA fragmentation is significantly reduced or even eliminated, which is an example of the present invention. If larger volumes of a sample should be required for fragmentation then the sample could be circulated through the focal point of the acoustic waves.

A much larger device is used in prior art, as shown with reference sign 200 in FIG. 1. A difference is that the prior art uses a transducer almost one order of magnitude larger than the one mentioned above in the context of the present invention. In the prior art larger volumes of aqueous samples around 200 µl are treated by actively moving the focal point of the transducer and increasing the incident power. Higher power requirements that scale with the size of the transducer combined with longer treatments times per run determine an upscale of the instrument for temperature control and electronics unit. These are disadvantages of the prior art.

Figure 2:
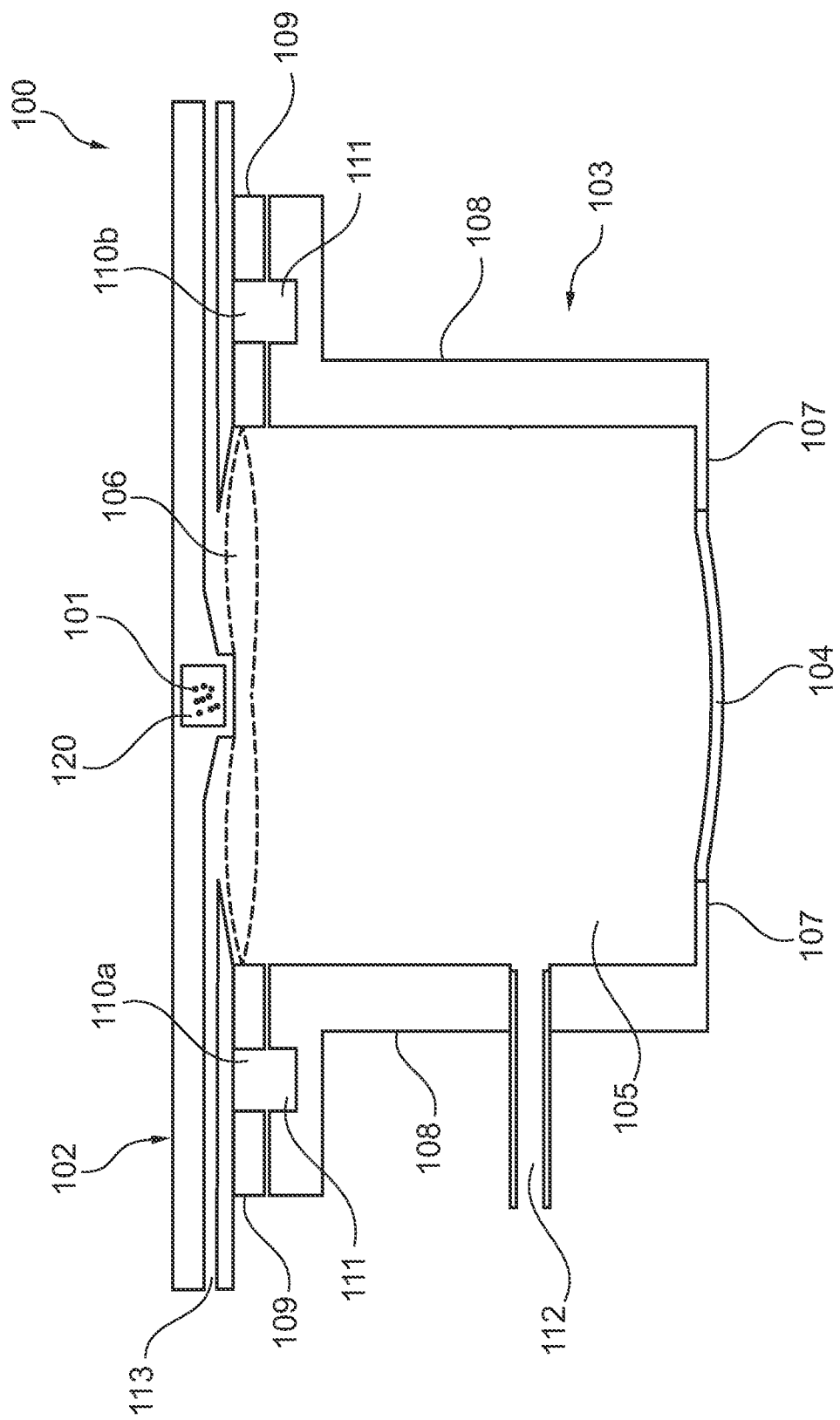
FIG. 2 schematically shows a device according to an exemplary embodiment of the invention.

FIG. 2 schematically shows a device 100 for fragmenting molecules in a sample 101 by ultrasound. The device comprises a cartridge 102 which is shown here exemplarily as a planar microfluidic cartridge. The device further comprises a fragmentation instrument 103 that provides for an ultrasound transducer 104. The device further comprises a fluid compartment 105 which in this embodiment is part of the fragmentation instrument 103. The cartridge comprises a sample compartment 120 in which the sample with the molecules to be treated is contained. It can clearly be seen that the fluid compartment 105 is spatially separated from the sample compartment 120, so as to preventing a mixture of the sample and the fluid which is filled in compartment 105. Furthermore, the cartridge and the fragmentation instrument fit together in such a way that a spatial closure of the fluid compartment 105 is established when the cartridge and the fragmentation instrument are assembled together. Furthermore, a sealing layer 109 is depicted in FIG. 2 which is placed between the cartridge and the fragmentation instrument. The sealing layer comprises apertures 110a and 110b for enabling an application of under-pressure between the fragmentation instrument and the cartridge. The fragmentation instrument comprises sidewalls 108 with at least one groove 111 building an under pressure channel or vacuum channel. The shown device 100 is adapted to apply under pressure through the groove 111 in order to suck the cartridge 102 onto the rims or sidewalls 108 of the fragmentation instrument. Thereby, a fluid-tight sealing is established and the opening 106, depicted with dotted lines, is entirely closed and separated from the spatial surrounding.

In other words, an ultrasound (shearing) unit with a sealing interface layer for working with a cartridge in which the material to be sheared is held is provided.

In other words, the opening is shut or delimited from the surrounding or separated from the surrounding by placing the cartridge on top of the fragmentation instrument. This may be done e.g. by sliding the cartridge onto the fragmentation instrument. Furthermore, the fragmentation instrument comprises a liquid inlet 112 and the cartridge comprises an overflow channel 113, so that flushing and drain off the fluid compartment 105 is possible. The cross-sectional view of FIG. 2 makes clear that the treatment of the sample 101 by ultrasound emitted from the transducer 104 is only possible when the volume of the fluid compartment 105 is closed by means of the cartridge.

As can be seen, the ultrasound transducer is placed at the bottom of the fragmentation instrument which may be out of plastics, glass or other material that can withstand the temperatures and the mechanical stress and/or strain during the ultrasound treatments. In experiments of short duration PMMA or polycarbonate could be the materials of choice. Also, composite materials could be used in order to best match above-mentioned requirements. The transducer 104 may have a range of operation close to 1 MHz so that the acoustical wavelength is comparable to the size of the sample compartment 120. The transducer may be of the size of 1-2 cm. Depending on the geometry, the transducer focal distance in water can be 4-5 cm. The water inlet/outlet 112 may be connected to a bidirectional mini pump. This mini pump (not shown) may also be comprised by the present invention. As can be seen from FIG. 2, the sample compartment 120 is located in the center of the cartridge 102 such that its location coincides with the focal volume of the transducer 104. The volume of the sample compartment may have a volume range between 50 and 100 µl, for example 4 mm×5 mm×5 mm.

Thereby the shown device and the shown fragmentation instrument, the cartridge and the method are able to fragment DNA to a desired length with a desired reproducibility by ultrasound.

As can be seen from FIG. 2, a unique solution for interfacing the cartridge 102 with the fragmentation instrument 103 is provided. As no active cooling is needed the fragmentation of molecules is improved. The need of active cooling is eliminated by controlling a combination of two factors. The first one is the acoustical energy that is converted into heat at the sample level. The second one is the time within which this energy is deposited. To be mentioned here is that the amplitude of the acoustic waves has to be large enough to satisfy the optimum conditions for bubble nucleation and subsequent cavitation processes specific to the sample used. For pure degassed water the amplitudes of the acoustic waves should correspond to sound intensity levels of $10^3$ W/cm$^2$. In our sample transducer configuration the optimum delivery of acoustical energy is obtained by applying a duty cycle such that the sample does not exceed a threshold temperature. The amount of water between the transducer and the sample is sufficient to absorb the heat from the sample level and the transducer. At the end of the treatment the water can be eventually evacuated for a next sample.

A much more compact product than current commercial products is provided by the present invention due to the reasons explained above.

If necessary, sensors can be placed on top of the overflow channel to provide feedback to the pump during loading the cell with fluid. A window can be placed on top of the cartridge to provide optical access. This can be an important feature of the device if the kinetics of a reaction is to be estimated. In addition dyes can be introduced in the sample fluid in order to monitor temperature or degree of mixing and/or fragmentation.

As can be seen from FIG. 2 this exemplary embodiment of the invention shows a fragmentation instrument that comprises sidewalls with at least one groove, wherein the device is adapted to apply under-pressure through said groove. Furthermore, the cartridge and the fragmentation instrument are respectively adapted in such a way that the cartridge can be sucked onto the sidewalls of the fragmentation instrument to thereby establish the closure of the fluid compartment.

Furthermore the sealing layer of FIG. 2 comprises apertures for enabling an application of under-pressure between the fragmentation instrument and the cartridge.

Therefore, in an assembled state, the cartridge may be sucked towards the fragmentation instrument by means of under-pressure which is applied by the fragmentation instrument and directed through the apertures of the sealing layer to mechanically act attractively on the surface of the cartridge. The apertures of the sealing layer may match with grooves of sidewalls and/or rims of the fragmentation instrument such that under-pressure is guidable from the grooves through the sealing layer to the surface of the cartridge.

After establishing the fluid-tight seal by assembling the cartridge and the ultrasound instrument together the space 105 is filled with a fluid e.g. water. And vice versa prior to taking the cartridge out at least some of the water in chamber 105 may be removed.

In other words, in case the substantially planar cartridge provides for an even surface which can be brought into mechanical contact with the rim of the fragmentation instrument which may be shaped e.g. as a tube. If the fluid-tight sealing is provided, the sealing layer together with the under-pressure provide for the prevention of a fluid leakage out of the fluid compartment by sucking and/or pressing the cartridge onto the rims of the housing of the fragmentation instrument. Subsequently, the ultrasound processing may start in order to fragment the molecules to a desired size or length.

FIG. 3 shows a cartridge 102 comprising a sample compartment 120 above which an optical window 116 is placed in order to get optical access for the user. The cartridge is provided with a soft contact layer that provides for a sealing layer 109. This sealing layer may be also gathered from following FIG. 4. There from it can be gathered that several apertures 110a, 110b, 110c, 110d, are comprised by the sealing layer 109 in order to enable the direction of under-pressure from the fragmentation instrument (not shown) to the surface of the cartridge 102. An overflow channel 113 is also comprised by the cartridge 102 of FIG. 3. As can be seen from FIG. 4, the sealing layer has a circular shape and has an opening 123 in the centre. The cartridge may have a rectangular or quadratic form but also a circular form or other forms are possible.

The sealing layer 109 placed between the cartridge and for example the rims of the fluid compartment (see FIG. 2 or FIG. 6) is provided in order to establish a fluid-tight sealing. Furthermore, this layer may provide for the feature of keeping the sample in place with respect to the focal point of the ultrasound transducer. As the sealing layer prevents liquid leakage out of the fluid compartment, no air is entering into the fluid compartment during experiment treatments. Therefore, the acoustic pattern is kept constant during ultrasound treatment and therefore a high reliability is provided by the sealing layer. Sealing may therefore be realized when vacuum or under-pressure is applied through to the holes placed in the sealing layer in combination to the channel grooves places on the rims of the fragmentation instrument. Experimental observations have shown that this is an efficient method suited for cartridges with plastics surfaces that can warp during the fabrication procedure, handling or as a result of local temperature changes.

Figure 5:
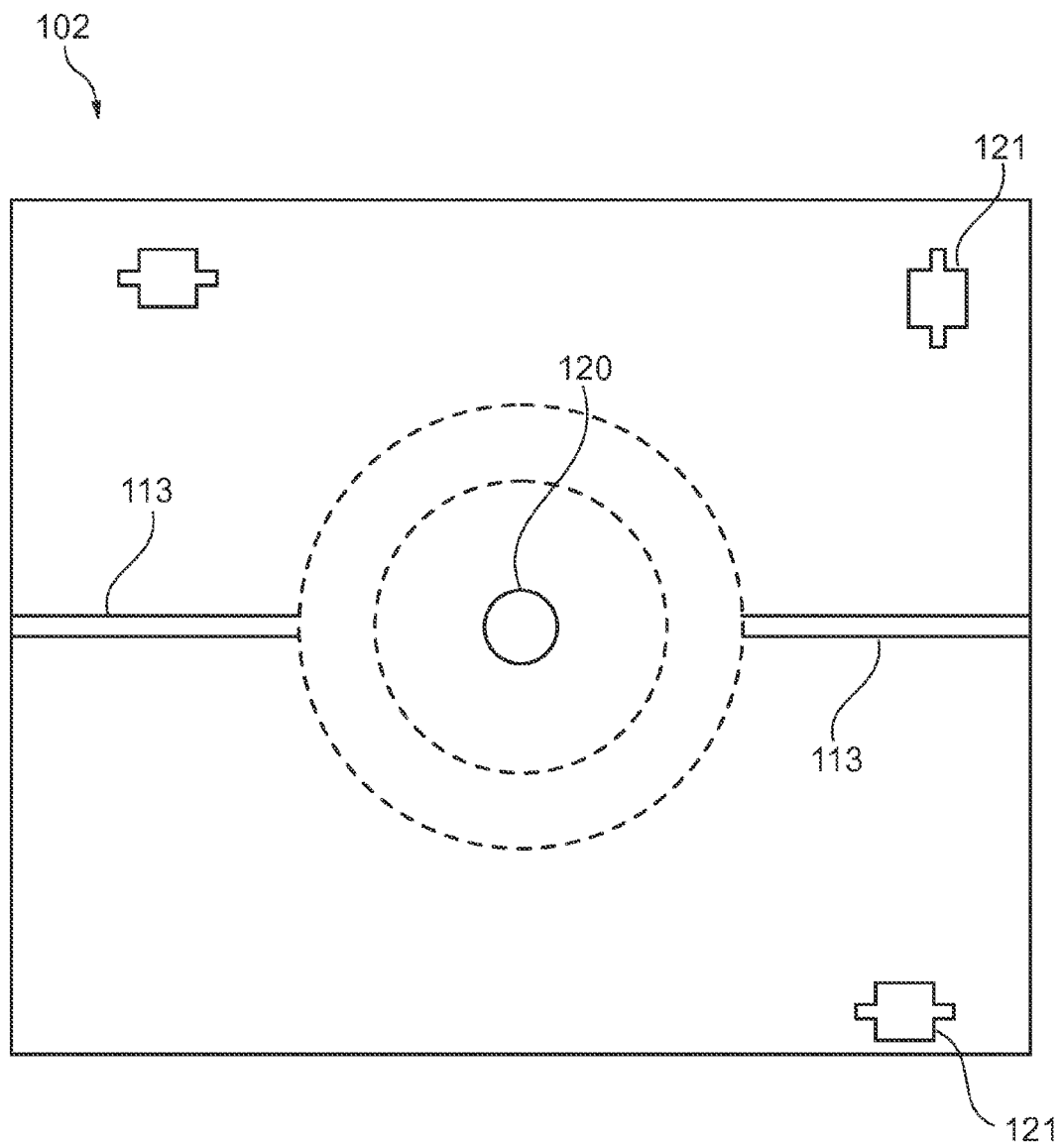
FIG. 5 schematically shows a top view of a cross-section of a cartridge according to an exemplary embodiment of the invention.

FIG. 5 is a top view of a cartridge 102 is given. Indicated with dotted lines, the overflow and air vent channels 113 are shown. Furthermore, alignment marks and/or indentations 121 are placed on the cartridge in order to ease the aligning of the sample compartment of the cartridge with respect to the ultrasound transducer (not shown) of the fragmentation instrument (not shown).

Figure 6:
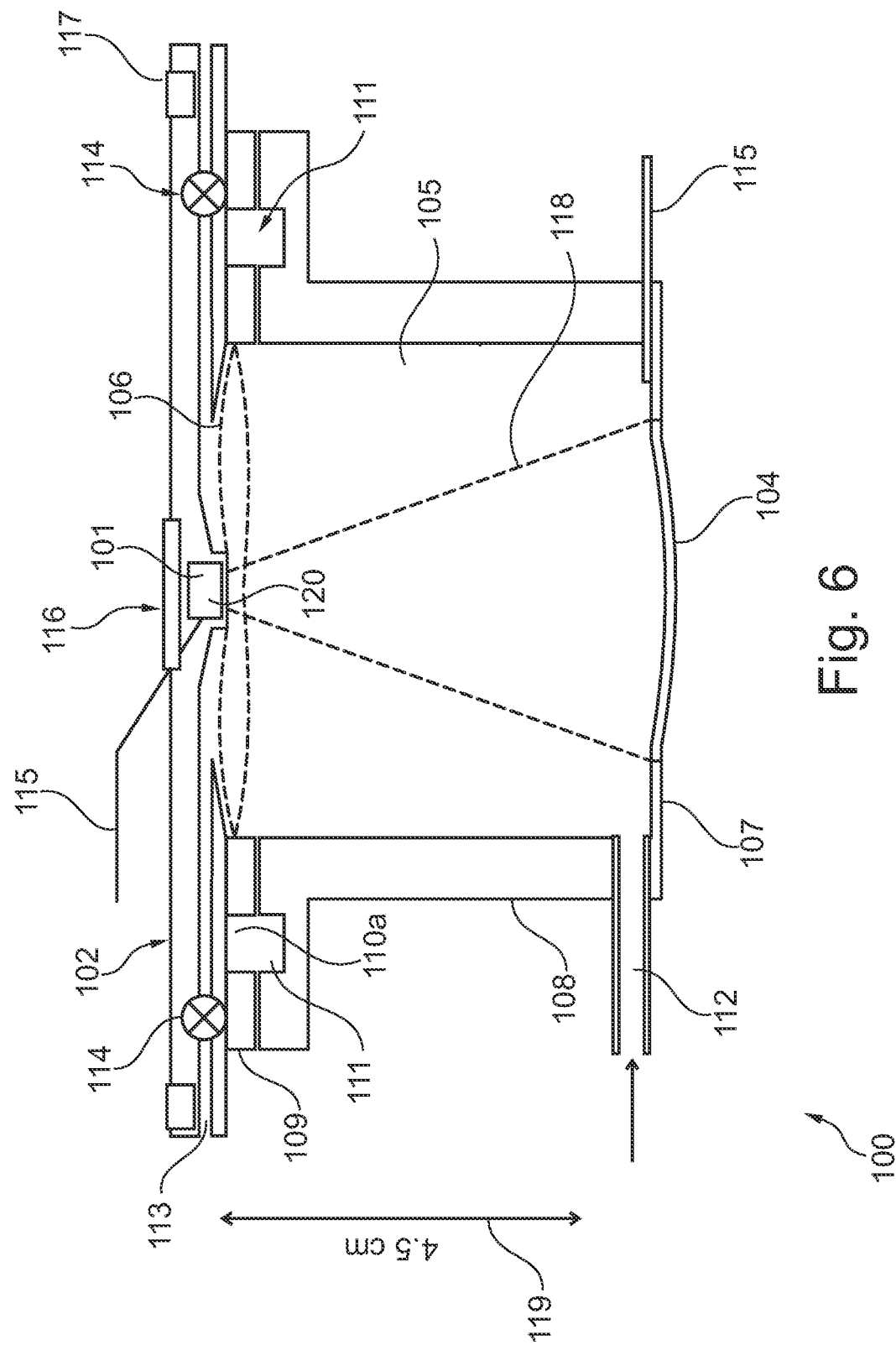
FIG. 6 schematically shows a device according to another exemplary embodiment of the invention.

FIG. 6 shows another exemplary embodiment of a device 100 for fragmenting molecules in a sample by ultrasound energy. FIG. 6 depicts the focused ultrasound energy beam 118 emitted by the transducer 104. Compared to FIG. 2 the liquid inlet 112 is based on the bottom 107 of the fragmentation instrument 103. Furthermore in addition to FIG. 2 an optical window 116 is provided by the cartridge 102 in order to provide optical axis. Furthermore, temperature probes 115 are depicted wherein the temperature probes are located at the sample compartment and in the fluid compartment. FIG. 6 further shows that the fluid compartment comprises an opening 106, depicted by the dotted lines, wherein the opening is fluid-tightly sealed due to the under-pressure that is applied through grooves 111 and through aperture 110a of the sealing layer 109 and therefore act as a pulling force on the surface of cartridge 102. The cartridge further comprises the overflow channel 113 as well as valves 114 within that channel. The valves 114 are part of the cartridge to close the water reservoir when it is e.g. fully filled. These may be pneumatically addressable valves. Alternatively, these valves can also consist of an air-permeable hydrophobic membrane that may consist of e.g. Gore Tex material. To protect the external vacuum pump the device has optionally container that collects any spilled water or water that leaked into the vacuum channel Regarding the pneumatically addressable valves the person skilled in the art without undue burden may make use of the technology for microfluidic cartridges with parallel pneumatic interfaces which he knows from WO 2011048521 A1. Thus, the cartridge of the present invention may comprise a three-dimensional fluid channel in which a fluid is to be transported by pneumatic pumping of a pneumatic instrument. Furthermore the microfluidic cartridge may comprise a flexible membrane, wherein the flexible membrane spans a plane and wherein the flexible membrane builds an outer surface of the cartridge. Additionally the three dimensional fluid channel is spatially defined in three dimensions by internal walls of the cartridge and by the flexible membrane, wherein the flexible membrane is in a ground state when no pressure or vacuum is applied to the flexible membrane. The flexible membrane is pneumatically deflectable from the ground state perpendicular to the plane of the flexible membrane in two directions when the cartridge is placed onto the parallel pneumatic interface plate. In other words the fluid is not transported over a flat surface but is moved along the three dimensional liquid channel. Furthermore the flexible membrane may be pneumatically deflectable in the areas which are part of the outer surface of the cartridge. In other words in a first region the flexible membrane spans the fluid channel which first region is part of the outer surface of the cartridge. According to this exemplary embodiment the flexible membrane may additionally extend in a second region under the outer surface of the cartridge, so that the membrane is not accessible from outside the cartridge in that second region. Furthermore the "ground state of the flexible membrane" describes the situation in which neither pressure nor vacuum is applied to the flexible membrane. Starting from this situation, the flexible membrane is deflectable towards the inner part of the cartridge and is also deflectable away from the cartridge. The cartridge, which may in this and in any other embodiment be for example a disposable cartridge, allows pneumatic actuation that is carried out through a reversible pneumatic interconnection between the pneumatic instrument and the cartridge, which interconnection is formed by the flexible membrane. Pneumatic drivers are integrated in the instrument for a low cost and reliable solution of the cartridge. The actuation of the fluid that is contained in the fluid channel within the cartridge is achieved by the deflection of the flexible membrane which may be attached to the major surface of the cartridge. Thus when the cartridge is attached to or inserted in the pneumatic interface plate compartments are formed by the flexible membrane of the cartridge and parts of the pneumatic interface plate. The pressure in these compartments, which pressure may be generated by the separate pneumatic instrument, determines the deflection of the flexible membrane which in turn actuates the fluid through which a movement is caused. This movement may also be used for the valve function. This microfluidic cartridge takes advantage of the high power and large stroke of pneumatic actuation while at the same time keeping the cartridge simple and at low costs, and allowing easy introduction of other physical transport across the interface plate like heat or acoustic vibration. It may be seen as an essential characteristic of the provided valve in the microfluidic cartridge to realize or stop/prevent the actuating of fluids in the cartridge by a pneumatic instrument. The facts, that the pneumatic driving makes use of a flexible cartridge membrane and that the pneumatic chambers underneath the membrane are reversibly assembled are important. This means, that the separation plane between the cartridge and the pneumatic instrument crosses the pneumatic chambers. The above described features, which might be part of the device according to the present invention and/or which features might also be part of the cartridge of the present invention and/or which features might also be part of the fragmentation instrument of the present invention will be described in a more detailed way with regard to FIG. 13.

Furthermore, in FIG. 6 a window 117 above the channel and close to the edge of the cartridge is provided wherein the window is adapted to provide for fluid sensing. The sealing layer 109 may be of PDMS. The rims 111 provide for a vacuum channel in order to establish the spatial closure of the fluid compartment when the cartridge and the fragmentation instrument are assembled together. As can be seen by the height information 119 this device may manufactured to have a height of 4.5 cm as an exemplary embodiment. Furthermore a pump (not shown) may be comprised by the cartridge to pump water into the fluid compartment.

Within FIG. 6 a device is shown which provides for a solution for mechanically couple a microfluidic cartridge with an ultrasonic transducer. This is realized by using a soft rubber-like interface between the cartridge and the walls of the cavity containing the transducer. This solution can be used to fragment DNA molecules in a closed (disposable) cartridge. The average size distribution of the DNA molecules fragmented in this way can be controlled by adjusting the amplitude of the acoustic waves created by the ultrasound transducer and by the duty cycle. No active cooling unit is required during the fragmentation of DNA molecules.

FIG. 7 shows a table of parameter of measurement with the measurement duration and the temperature change as entries.

Figure 8:
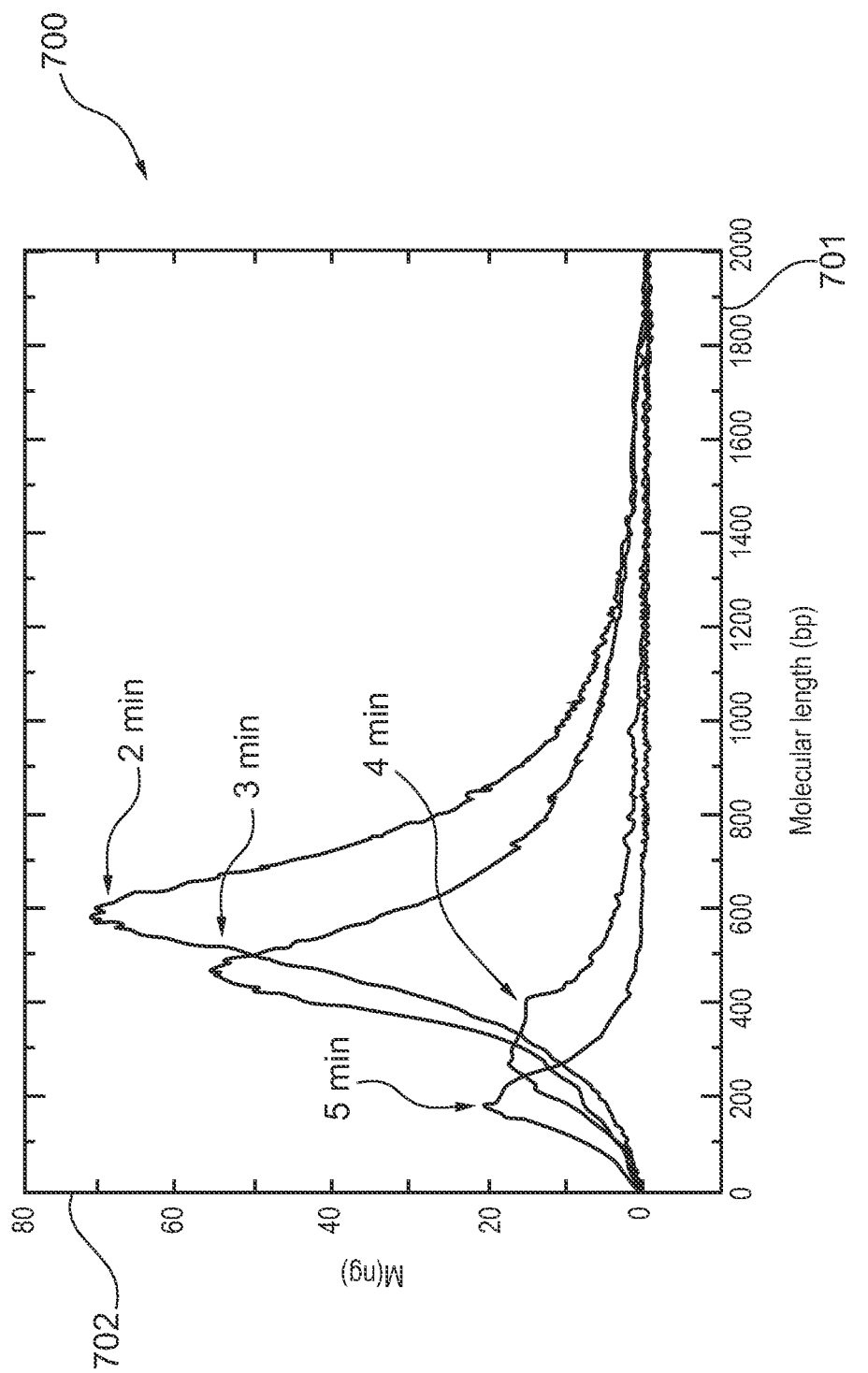
FIGS. 8 and 9 show experimental results of fragmentation of DNA with the present invention.
Figure 9:
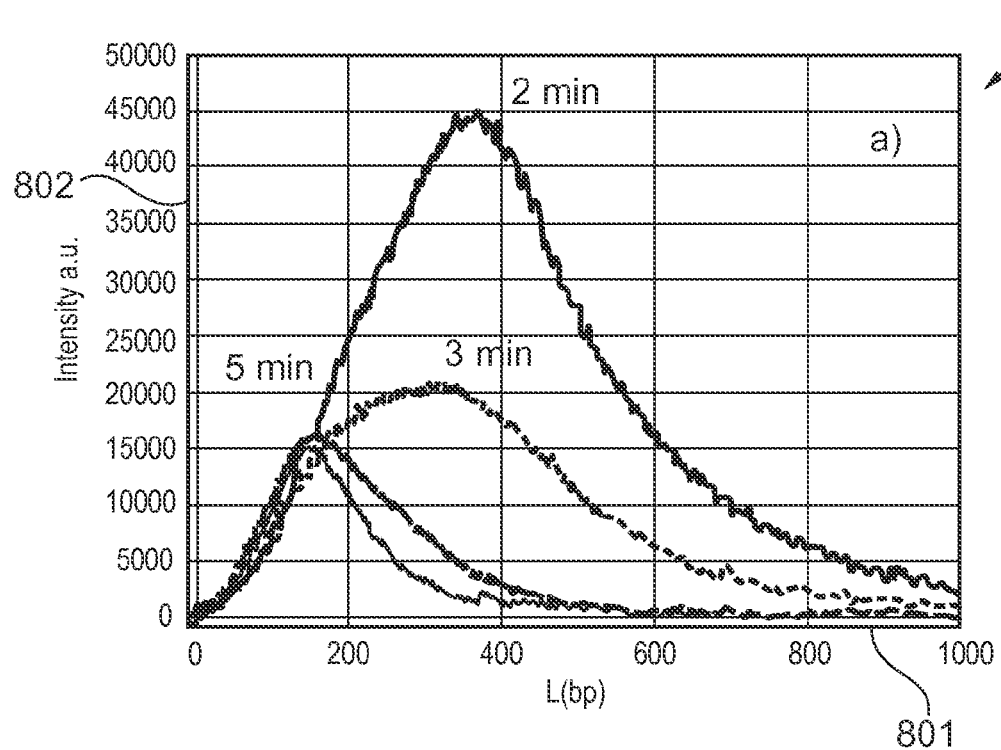

FIGS. 8 and 9 provide for experimental results obtained with the device as described with respect to FIG. 6. These results are described herein in order to demonstrate that effective DNA fragmentation is achieved by the device of the present invention. An exemplary embodiment of the device had a height of 4.5 cm and a cross-sectional surface of approximately 1 cm². Therefore, with a volume of 4.5 cm³ such a DNA fragmentation was achieved without active cooling. These results prove the potential of integrating ultrasound fragmentation following the principles as described above and below.

Figure 11:
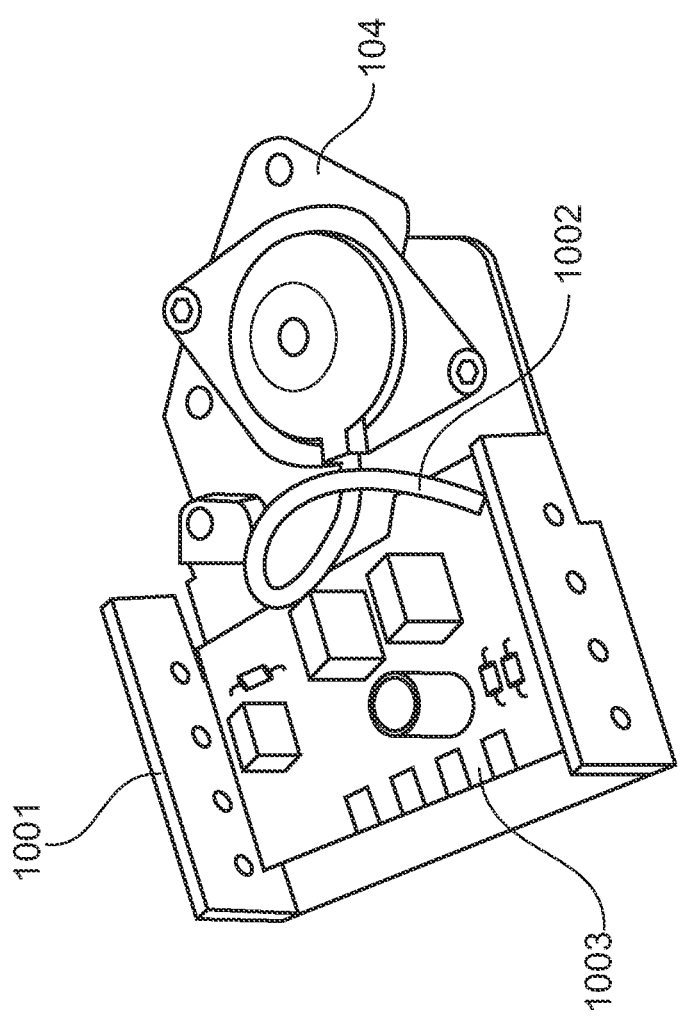
FIG. 11 schematically shows an ultrasound transducer used in an exemplary embodiment of the present invention.

For the results of FIGS. 8 and 9 the following experimental setups were made. The transducer used was operated at 1.7 MHz and connected to a wide band power amplifier ENI (50 dB). The RF amplifier had a maximum input voltage of $1V_{RMS}$ and an input/output impedance of 50Ω. The input voltage was provided by function generator where burst period and the number of cycles per burst was adjusted. It should be noted that although the power supply used in the shown experiments is rather large, offering the required flexibility, a much smaller foot print of the driving electronics is possible. The used transducer is shown in FIG. 11.

It was chosen burst periods of 585 μs with 200 per burst at 1.7 MHz. The input voltage was 800 $mV_{RMS}$. In the table show in FIG. 7 it is indicated the duration of treatments and the temperature measures in the proximity of the transducer. As can be seen for the duration of the experiments the temperature did not exceed critical values that can render changes in operation. Also temperature measurements (not shown here) taken in the sample compartment did not exceed 70° C. The sample volumes were 100 μl with a starting nucleic acid concentration of 65 ng/μl. Therefore it is concluded that no active cooling is required for the proposed fragmentation procedure.

After the treatment procedure the samples were analyzed by gel electrophoresis. Commercial ladders were used in order to quantify the migration distances from pixels into molecular length in bp. It can be seen that within these operation conditions $L_{AVG}$=200 bp can be obtained which is an advantage of the present invention due to the need described above.

In FIG. 8 size distribution of fragmented DNA molecules by the present invention is shown in diagram 700 thereby molecular length is shown on the horizontal axis 701 and the quantity is depicted on the vertical axis 702.

Figure 10:
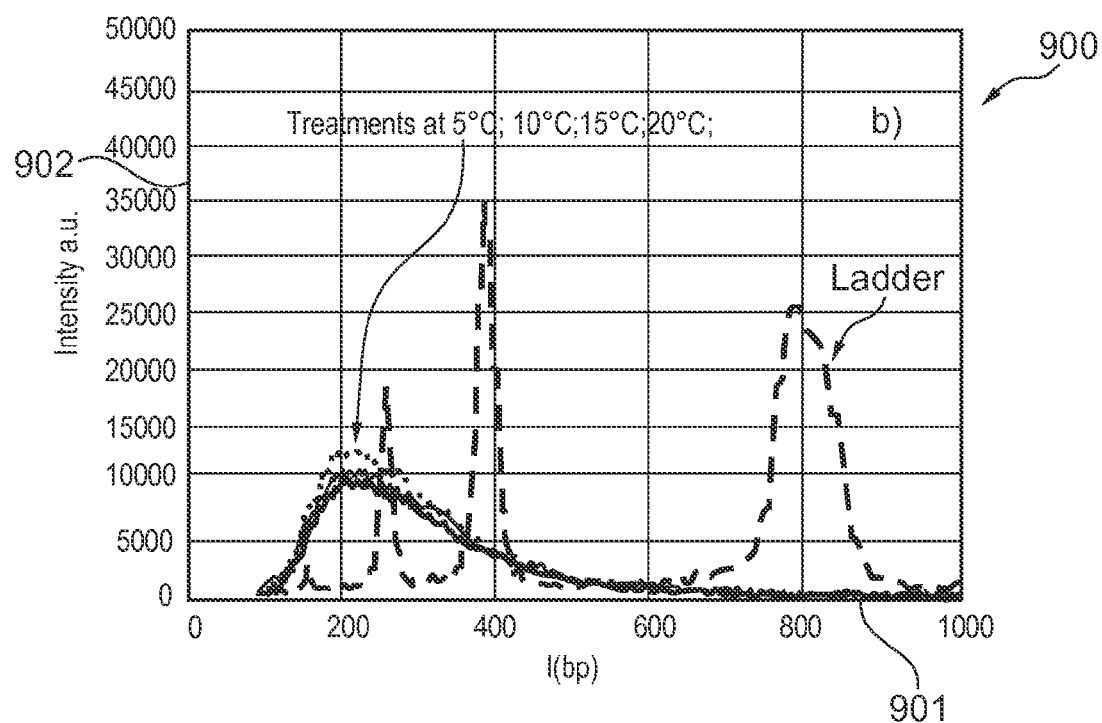
FIG. 10 shows results obtained with an instrument of the state-of-the-art.

In both FIGS. 9 and 10 diagrams 800 and 900 are shown in which the length of the molecules is respectively depicted by the horizontal axis 801 and 902. The vertical axis 802 and 902 show the used intensity of the ultrasound in arbitrary units.

The comparison between FIG. 9 and FIG. 10 depicts a comparison between the size distribution results obtained with a device and/or method according to the present invention, i.e. FIG. 9, and the ones obtained with prior art, FIG. 10. The time dependent measurement sequence was performed in similar conditions as indicated above. The treatments performed with the prior art device were taken for the same time interval (5 minutes with a power input of 18 W as indicated by the instrument panel and 20% duty cycle). Noticeable is the fact that changing the temperature does not change the output of the treatment significantly. This can be understood within the classical nucleation theory where the bubble nucleation is described as following Boltzmann statistics. The data presented in FIGS. 9 and 10 has been obtained with samples with the same initial DNA concentration before the treatments and the same conditions for performing the electrophoresis measurements. In both measurements the same exposure times were used.

FIG. 11 shows a transducer 104 with a housing 1001, electrical supply line 1002 as well as an electrical circuit 1003.

Figure 12:
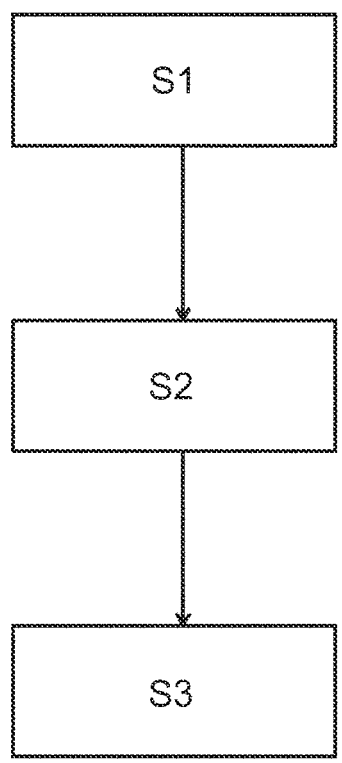
FIG. 12 schematically shows a flow diagram of a method according to an exemplary embodiment of the present invention.

FIG. 12 schematically depicts a flow diagram of a method according to an embodiment of the present invention. The shown method for providing an ultrasound device for fragmenting molecules in a sample comprises as a first step providing for a device which comprises a fragmentation instrument, a cartridge and a fluid compartment. This first step is depicted with S1. The second step, S2, is the placing of the cartridge onto the fragmentation instrument. Thereby, the cartridge comprises a sample compartment which is spatially separated from the fluid compartment. As a third step S3 is shown which is causing a closure of the fluid compartment by the placing of the cartridge onto the fragmentation instrument.

If desired, the method may comprise also one or more of the following steps. Applying an under pressure between the cartridge and the fragmentation instrument, and sucking the cartridge towards the instrument by means of the under pressure.

Furthermore, if desired, the method may further comprise the step of providing for a seal layer between the fragmentation instrument and the cartridge and sealing the fluid compartment substantially fluid tight by applying under pressure.

In another exemplary embodiment the method may comprise the steps of opening a valve of a channel in the cartridge, transporting liquid into the liquid compartment, closing the valve, generating ultrasound thereby fragmenting molecules in the sample, opening the valve and evacuating the liquid from the liquid compartment.

Furthermore an alternative exemplary embodiment of the present invention may be a method for treating molecules like DNA with ultrasound as follows: placing the cartridge on top of the fluid compartment of the fragmentation instrument. For instance this can be done by sliding. Further, applying vacuum is in order to provide sealing effect, opening the valves at the top of the device and pumping liquid in the fluid compartment. Further the step of stopping the pumping, when the water reaches the window for fluid sensing. Subsequently powering the ultrasound transducer according to a desired scheme may be performed. Opening the valves at the top of the device to allow evacuating the fluid from the fluid compartment may be done next. Further, the step of evacuating the fluid from the fluid compartment by reversing the flow generated by the pump. Further stopping the vacuum pump may be an optional step. This is the end of DNA fragmentation.

The power delivery scheme depends on preliminary experiments. The transducer may be powered such that the parameters like duty cycle and number of cycles per period can be varied.

Figure 13:
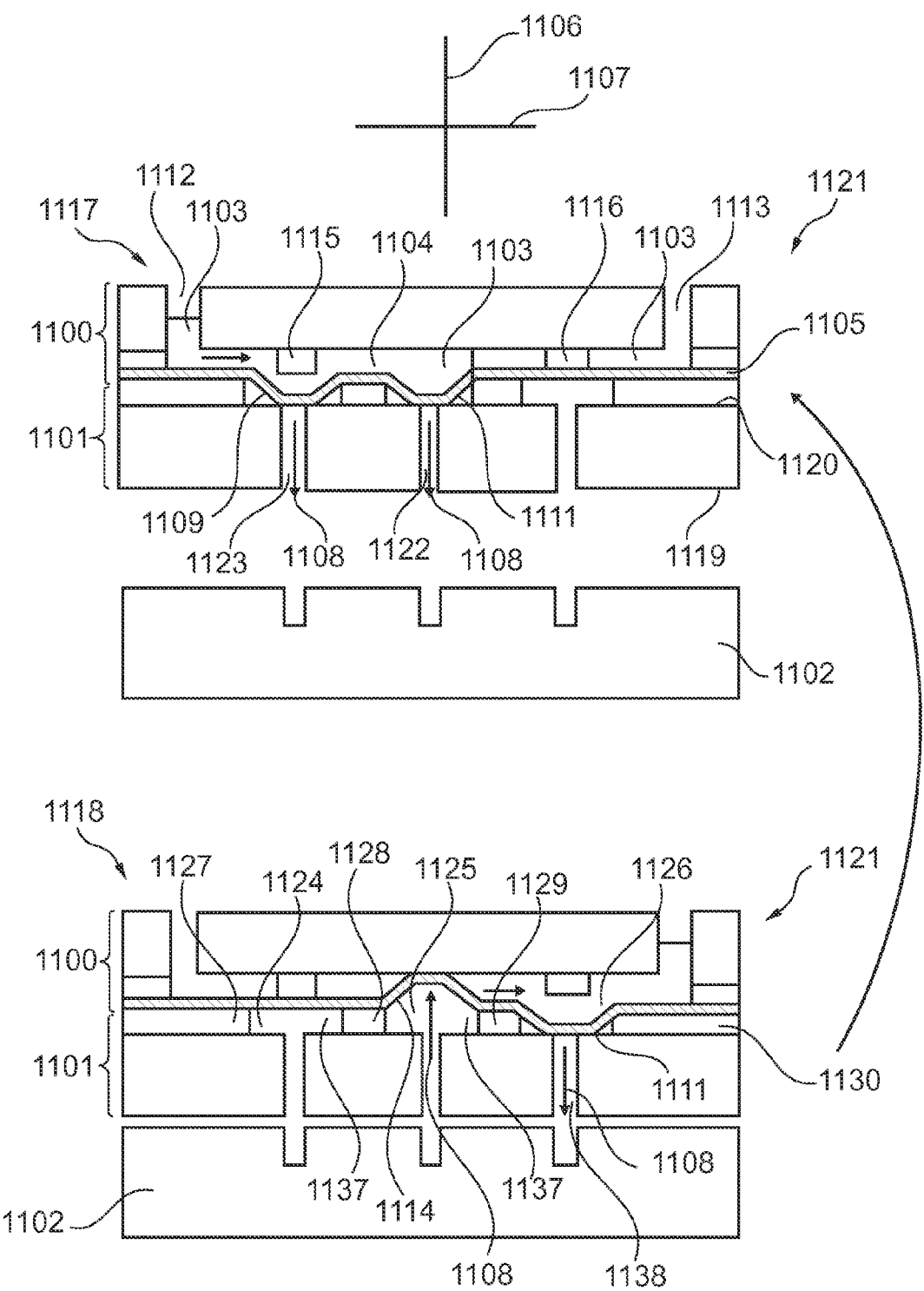
FIG. 13 schematically shows a microfluidic cartridge, a pneumatic interface plate and a pneumatic instrument which can be used in combination with the present invention.

FIG. 13 shows a cartridge 1100 which fits together with the fragmentation instrument (not shown in FIG. 13) like e.g. the fragmentation instrument of FIG. 6 in such a way that a spatial closure of the fluid compartment of fragmentation instrument is established when the cartridge and the fragmentation instrument are assembled together. FIG. 13 shows in the upper part a system 1121 for fluid actuation inside a microfluidic cartridge 1100 in a first state wherein the lower part of FIG. 13 shows such a system 1121 in a second state, in which the contained fluid 1104 inside the cartridge has been transported. Both shown systems 1121, the upper and the lower one, consist of the same elements.

Furthermore FIG. 13 shows a microfluidic cartridge 1100 for being inserted in the parallel pneumatic interface plate 1101 of a pneumatic instrument wherein the cartridge comprises a three-dimensional fluid channel 1103 in which a fluid 1104 is to be transported. Such a parallel pneumatic interface plate 1101 may be for example part of the fragmentation instrument (not shown). However the parallel pneumatic interface plate may also be a component which is physically separated from the cartridge and the fragmentation instrument but may be integrateable into one of the latter. Furthermore the cartridge 1100 comprises a flexible membrane 1105 wherein the flexible membrane spans a plane. The plane spans along the direction 1107. Furthermore the flexible membrane builds an outer surface of the cartridge wherein the fluid channel is spatially defined by walls of the cartridge and by the flexible membrane. Furthermore the flexible membrane is in a relaxed state when no over pressure, under pressure or vacuum is applied to the flexible membrane. The flexible membrane is pneumatically deflectable from the relaxed state perpendicular to the plane of the flexible membrane in two directions. In other words, the membrane 1105 can be directed in the direction 1106 firstly in the upwards and secondly in the downwards orientation.

Furthermore it can be seen that the flexible membrane is deflected at several points 1109 and 1110 by pneumatic pumping 1108. Thereby pneumatic pumping means that an over pressure and/or an under pressure is applied to the membrane in the pneumatic chambers like e.g. 1137. The external pneumatic instrument 1102 may create such a pneumatic pumping 1108. The external pneumatic instrument 1102 may be part of the fragmentation instrument (not shown) but may also be an external device. By applying a corresponding under pressure at the two pneumatic channels 1122 and 1123 within the pneumatic interface plate 1101 the flexible membrane 1105 is sucked into the recesses above these pneumatic channels. By changing the pressure situation within the pneumatic channels of the pneumatic interface plate, which is shown at the lower figure of FIG. 13 the flexible membrane is pressed towards the inner side of the cartridge at the middle pneumatic channel of the cartridge. Additionally under pressure is applied at the pneumatic channel 1138 on the right hand side so that the fluid is transported from the left-hand side of FIG. 13 to the right-hand side of FIG. 13 inside the fluid channel. This mechanical principle may inter alia be used for the device shown in FIG. 1 and FIG. 6.

As can be seen from FIG. 13 the interface plate has an instrument side 1119 which faces to the instrument when the interface plate is inserted into the instrument 1102. Furthermore the interface plate has a cartridge side 1120 which faces to the cartridge when the cartridge is inserted into the interface plate. Pneumatic channels 1122, 1123 and 1138 are provided to connect the pneumatic fluid like for example air from the instrument side to the cartridge side to enable pneumatic driving of the flexible membrane of the microfluidic cartridge. The recesses 1124 to 1126 allow the sucking of the flexible membrane into the recesses. As can be seen in the lower part of FIG. 13 in the middle pneumatic channel 1122 the membrane closes the fluid channel to provide for a valve 1114 inside the fluid channel.

By applying such a method with sequentially applying over pressure and/or under pressure in a corresponding way the fluid is transportable from the beginning 1112 of the fluid channel to the end 1113 of the fluid channel within the microfluidic cartridge.

It can be seen that the cartridge side of the interface plate has a step-like surface with recesses and pneumatic channels that are formed in a T-shape like way when looked onto the pneumatic channels and recesses in a cross-section.

In other words, this embodiment provides for a cartridge comprising an external flexible membrane covering a fluid path. After insertion of the cartridge into the instrument, the membrane can locally deflected by pneumatics of the instrument such that the fluid is moved along the fluid path. This can be used to transport the sample 120 into the sample compartment 101 of a cartridge 102 shown in FIG. 1 and FIG. 6. The membrane may locally be sucked away from or pushed towards the cartridge creating a changing volume in the fluid path which is the fluid channel for the sample and under the membrane. Thus, the fluid is transported through the cartridge. The cartridge may comprise walls that together with the flexible membrane define the changing volume through which the fluid can be transported.

It has to be noted that exemplary embodiments of the invention are described with reference to different subject matters. In particular, some exemplary embodiments are described with reference to apparatus type claims whereas other exemplary embodiments are described with reference to method type claims. However, a person skilled in the art will gather from the above and the following description that, unless otherwise notified, in addition to any combination of features belonging to one type of subject matter also any combination between features relating to different subject matters, in particular between features of the apparatus type claims and features of the method type claims, is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for fragmenting molecules including DNA or nucleic acids in a sample by ultrasound, the device comprising:
    a cartridge having a sample compartment for including the sample with the molecules;
    a fragmentation instrument with an ultrasound transducer; and a fluid compartment containing a fluid for transmitting the emitted ultrasound from the ultrasound transducer to the sample, wherein the fragmentation instrument is configured to fragment the DNA or nucleic acids by the ultrasound emitted from the ultrasound transducer and propagated through the fluid in the fluid compartment to the sample included in the sample compartment, wherein the fluid compartment is spatially separated from the sample compartment, wherein the cartridge and the fragmentation instrument are configured to fit together in such a way that a spatial closure of the fluid compartment is established when the cartridge and the fragmentation instrument are assembled together, wherein the cartridge has a planar shape, and wherein the fragmentation instrument has a vessel-like shape.

2. The device according to claim 1, wherein the fluid compartment comprises an opening, and wherein the cartridge and the fragmentation instrument are respectively configured to establish a closure of the fluid compartment in such a way that the opening of the fluid compartment is fluid tightly sealed.

3. The device according to claim 1, wherein the fluid compartment is comprised by the fragmentation instrument, wherein the fluid compartment comprises a bottom and at least one side wall, and wherein the fluid compartment comprises an opening opposite the bottom.

4. The device according to claim 1, further comprising a sealing layer in between the cartridge and the fragmentation instrument.

5. The device according to claim 4, wherein the sealing layer comprises apertures for enabling an application of under pressure between the fragmentation instrument and the cartridge.

6. The device according to claim 1, wherein the fragmentation instrument comprises sidewalls with at least one groove, wherein the device is configured to apply under pressure through the groove, and wherein the cartridge and the fragmentation instrument are respectively adapted in such a way, that the cartridge can be sucked onto the sidewalls of the fragmentation instrument to thereby establish the closure of the fluid compartment.

7. The device according to claim 1, wherein the fragmentation instrument comprises a liquid inlet, and wherein the cartridge comprises an overflow channel.

8. The device according to claim 4, wherein the sealing layer is a flexible membrane, wherein the flexible membrane provides for the spatial closure of the fluid compartment, and wherein the flexible membrane is configured to actuate the sample comprised in the sample compartment when the ultrasound transducer emits the ultrasound.

9. A method for providing an ultrasound device for fragmenting molecules including DNA or nucleic acids in a sample, the method comprising the acts of:

fitting together a cartridge and a fragmentation instrument having a fluid compartment to established a spatial closure of the fluid compartment, wherein the cartridge has a sample compartment for including the sample with the molecules, and wherein the fluid compartment is spatially separated from the sample compartment; and providing an ultrasound transducer for emitting ultrasound from the ultrasound transducer that propagate through fluid in the fluid compartment to the sample included in the sample compartment for fragmenting the DNA or nucleic acids by the ultrasound, wherein the sample compartment is spatially separated from the fluid compartment, wherein the cartridge has a planar shape, and wherein the fragmentation instrument has a vessel-like shape.

10. The method according to claim 9, further comprising the act of:

applying an under pressure between the cartridge and the fragmentation instrument; and sucking the cartridge towards the fragmentation instrument by the under pressure.

11. The method according to claim 9, further comprising the acts of:

providing for a seal layer between the fragmentation instrument and the cartridge; and sealing the fluid compartment substantially fluid tight by applying under pressure.

12. The method according to claim 9, further comprising the acts of:

opening a valve of a channel in the cartridge;

transporting the sample through the channel into the sample compartment;

closing the valve;

generating ultrasound thereby fragmenting the molecules in the sample;

opening the valve; and evacuating the sample from the sample compartment.

* * * * *